United States Patent [19]

Gupta

[11] Patent Number: 4,709,102

[45] Date of Patent: Nov. 24, 1987

[54] PROCESS FOR PRODUCING 2-LOWER ALKYL PHENOLS

[75] Inventor: Balaram B. G. Gupta, N. Plainfield, N.J.

[73] Assignee: Celanese Corporation, New York, N.Y.

[21] Appl. No.: 916,269

[22] Filed: Oct. 7, 1986

[51] Int. Cl.$^4$ ............................................. C07C 37/48
[52] U.S. Cl. .................................. 568/780; 568/783; 568/789
[58] Field of Search ................ 568/780, 789, 794, 783

[56] References Cited

U.S. PATENT DOCUMENTS

| | | | |
|---|---|---|---|
| 4,278,816 | 7/1981 | Shim | 568/780 |
| 4,447,657 | 5/1984 | Firth et al. | 568/783 |
| 4,465,871 | 9/1984 | Firth et al. | 568/783 |
| 4,476,330 | 10/1984 | Kerr et al. | 568/783 |
| 4,538,008 | 9/1985 | Firth et al. | 568/783 |

FOREIGN PATENT DOCUMENTS 2345911  9/1973  Fed. Rep. of Germany ...... 568/783

OTHER PUBLICATIONS

Dewar et al., "Jour. Chem. Society", pp. 959–963, (1960).

*Primary Examiner*—Werren B. Lone

[57] ABSTRACT

The production of a 2-lower alkyl phenol, e.g., 2-cresol or 2-ethylphenol, is carried out by transalkylation of a lower alkyl phenyl ether, e.g. anisole or phenetole, at an elevated temperature in the presence of a medium pore, pentasil-type molecular sieve, e.g. an H-ZSM-5 zeolite, a silicalite or an AMS-1B borosilicate, as catalyst.

18 Claims, No Drawings

PROCESS FOR PRODUCING 2-LOWER ALKYL PHENOLS

This invention relates to a process of producing 2-lower alkyl phenols such as 2-cresol and 2-ethylphenol.

BACKGROUND OF THE INVENTION 2-lower alkyl phenols such as 2-cresol and 2-ethylphenol are useful in a variety of applications. Thus, they may be used as disinfectants and solvents and as intermediates in the formation of phenolic anti-oxidants and triaryl phosphates, e.g. by reaction with phosphorus oxychloride. Moreover, 2-ethylphenol can be readily dehydrogenated to 2-vinylphenol which is a useful monomer in the preparation of certain polymers.

Various zeolites and zeolite-type materials are known in the art for the catalysis of chemical reactions. For example, U.S. Pat. No. 3,702,886, of Argauer, discloses a class of synthetic zeolites, characterized as "Zeolite ZSM-5", which are effective for the catalysis of certain hydrocarbon conversion processes.

U.S. Pat. No. 4,061,724 of Grose et al discloses various synthetic crystalline silica polymorphs or "silicalites" which are stated to be useful in selectively adsorbing organic materials from water.

U.S. Pat. No. 4,285,919 of Klotz et al discloses certain crystalline borosilicates, i.e. "AMS-1B" borosilicates which are stated to be useful as catalysts for various hydrocarbon conversion processes.

U.S. Pat. No. 4,371,714 of Young discloses a process for the alkylation of phenol or its alkyl ethers in the presence of a particular type of zeolite catalyst, e.g. ZSM-5, to produce a product rich in 4-alkylphenyl alkyl ethers.

U.S. Pat. No. 4,532,368 of Swanson et al discloses a process for making a mixture of meta- and para-alkylphenols by contacting a mixture of phenol, ortho-alkylphenol and an alkylating agent with a zeolite such as ZSM-5 under alkaline conditions.

U.S. Pat. No. 3,354,221 of Landis et al discloses the use of various crystalline aluminosilicate zeolites as catalysts for the Fries rearrangement of phenolic esters to hydroxy aromatic ketones.

Japanese Patent Publication (Early Disclosure) No. 85-252436 discloses a process for the preparation of acylphenols by reacting a phenol, e.g. phenol, ortho-cresol or ortho-ethylphenol, with a carboxylic acid in the presence of an ion-exchange layered clay catalyst, e.g. synthetic mica, montmorillonite or vermiculite.

Applicant's pending application Serial No. 803,194, filed Dec. 2, 1985, teaches the use of ZSM-5 zeolites as catalysts for the reaction of phenol and a lower alkanoic acid, e.g. acetic acid, to form a 2-hydroxyphenyl lower alkyl ketone such as 2-hydroxyacetophenone.

Pending application Ser. No. 803,195, filed Dec. 2, 1985 by Nicolau et al, teaches the use of silicalites as catalysts for reactions similar to those disclosed in application Ser. No. 803,194 described in the preceding paragraph.

Applicant's pending application Ser. No. 844,641, filed Mar. 27, 1986, teaches the reaction of a lower alkyl- or phenyl substituted benzene, e.g., toluene, ethylbenzene or biphenyl, with a lower alkanoic acid, e.g., acetic acid, in the presence of a medium-pore, pentasil-type molecular sieve, e.g. a ZSM-5 zeolite, to produce a 4-lower alkyl- or 4-phenyl ring-substituted phenyl lower ketone, e.g., 4-methylacetophenone, 4-ethylacetophenone, or 4-phenylacetophenone.

Applicant's pending application Ser. No. 883,675, filed July 9, 1986, teaches the reaction of phenol with a lower acetal or ketal, e.g., 1,1-dimethoxyethane, in the presence of a protonated, i.e. hydrogen form of a ZSM-5 zeolite catalyst, to produce a 1-hydroxy-2-lower alkoxyalkyl benzene such as 2-(1'-methoxyethyl) phenol.

SUMMARY OF THE INVENTION

In accordance with this invention, a lower alkyl phenyl ether, e.g. anisole or phenetole, is transalkylated in the presence of a medium-pore, pentasil-type molecular sieve, to produce a 2-lower alkyl phenol, e.g. 2-cresol or 2-ethylphenol.

DESCRIPTION OF SPECIFIC EMBODIMENTS

The transalkylation of the lower alkyl phenyl ether to form a 2-lower alkyl phenol proceeds in accordance with the following equation:

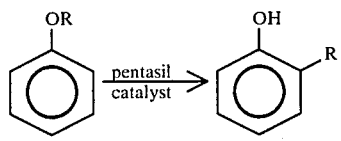

where R is lower alkyl, e.g. containing 1 to 4 carbon atoms in straight or branched chain. R may be, for example, methyl, ethyl, n-propyl, isopropyl, n-butyl or isobutyl.

As stated, the catalyst for the reaction is a medium pore, pentasil-type molecular sieve. In general, such catalysts are crystalline silicates containing a configuration of linked tetrahedra consisting of eight to twelve five-membered rings and a channel system which is three-dimensional and defined by somewhat elliptical ten-membered rings of tetrahedra, and consists of interesting straight and sinusoidal channels. Many of the silicates contemplated as catalysts under this invention have pores in the range of about 5 to 8 Angstrom units in diameter. Moreover, they often have similar although not necessarily identical X-ray diffraction patterns but have at least the following significant lines (i.e. interplanar spacings) in Table I, wherein "s"=strong, "w"=weak, "v.s."=very strong, and "m"=medium:

TABLE I

| Interplanar Spacing d(A): | Relative Intensity |
| --- | --- |
| 11.2 ± 0.2 | w-vs |
| 10.0 ± 0.2 | w-vs |
| 6.04 ± 0.1 | w-m |
| 5.97 | |
| 3.82 ± 0.1 | vs |
| 3.7 ± 0.05 | ms-s |
| 2.99 ± 0.02 | w-m |

One class of pentasil type catalysts contemplated under this invention are the H-ZSM-5 zeolites of which are prepared by replacing with hydrogen ions most of the cations of a ZSM-5 zeolite, the composition, characteristics and preparation of which are set out in the previously cited U.S. Pat. No. 3,702,886 of Argauer, the entire disclosure of which is incorporated by reference.. These ZSM-5 zeolites have the following formula:

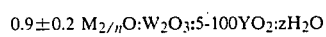

$$0.9 \pm 0.2\ M_{2/n}O : W_2O_3 : 5\text{-}100 YO_2 : zH_2O$$

wherein M is a cation, n is the valence of said cation, W is selected from the group sonsisting of aluminum and gallium, Y is selected from the group consisting of silicon and germanium, and z is from 0 to 40. In a preferred synthesized form, the zeolite has a formula, in terms of mole ratios of oxides, as follows:

$$0.9 \pm 0.2 M_{2/n}O:Al_2O_3:5\text{-}100SiO_2:zH_2O$$

and M is selected from the group consisting of a mixture of alkali metal cations, especially sodium, and tetraalkyl-ammonium cations, the alkyl groups of which preferably contain 2-5 carbon atoms. In a particularly preferred class of catalysts for purposes of the present invention, the molar ratio of $SiO_2$ to $Al_2O_3$ in the latter formula is within the ratio of about 20 to 60.

The ZSM-5 zeolites in most cases have a distinguishing crystalline structure yielding an X-ray diffraction pattern determined as described in U.S. Pat. No. 2,702,886, with significant lines as indicated in Table II, wherein "s"=strong, "w" weak and "v.s."=very strong.

TABLE II

| Interplanar Spacing d(A): | Relative Intensity |
|---|---|
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 ± 0.1 | w. |
| 5.97 | |
| 5.56 ± 0.1 | w. |
| 5.01 ± 0.1 | w. |
| 4.25 ± 0.06 | w. |
| 3.85 ± 0.07 | v.s. |
| 3.71 ± 0.05 | s. |
| 3.04 ± 0.03 | w. |
| 2.99 ± 0.02 | w. |
| 2.94 ± 0.02 | w. |

The active catalyst of this type which may be utilized in the process of the present invention, is characterized as an "H-ZSM-5" zeolite and is prepared from a "ZSM-5" zeolite by replacing most, and generally at least about 80% of the cations of the latter zeolite with hydrogen ions using techniques well-known in the art.

Another class of pentasil type silicates which may be utilized as catalysts in the process of this invention are the "silicalites" which are crystalline silica polymorphs, many of which are similar to those described, for example, in previously-cited U.S. Pat. No. 4,061,724 issued to Grose et al on Dec. 7, 1977, the entire disclosure of which is incorporated by reference.

The X-ray powder diffraction pattern of many of the silicalites utilized in the present invention (600 degrees C. calcination in air for one hour) has as its six strongest lines (i.e. interplanar spacings) those set forth in Table III below, wherein "S"=strong and "VS"=very strong.

TABLE III

| d-A | Relative Intensity |
|---|---|
| 11.1 ± 0.2 | VS |
| 10.0 ± 0.2 | VS |
| 3.85 ± 0.07 | VS |
| 3.82 ± 0.07 | S |
| 3.76 ± 0.05 | S |

TABLE III-continued

| d-A | Relative Intensity |
|---|---|
| 3.72 ± 0.05 | S |

The silicalites utilized as catalysts in the present invention have in the as-synthesized form a specific gravity at 25° C. of 1.99±0.08 g/cc as measured by water displacement. In the calcined (600° C. in air for 1 hour) form silicalite has a specific gravity of 1.70±0.08 g/cc. With respect to the mean refractive index of silicalite crystals, values obtained by measurement of the as-synthesized form and the calcined form (600° C. in air for 1 hour) are, respectively, 1.48±0.01 and 1.39±0.01.

Crystals of silicalite in both the as-synthesized and calcined form are orthorhombic and have the following unit cell parameters: a=20.05 A, b=20.0 A, c=13.4 A, with an accuracy of ±0.1 A on each of the above values. The pore diameter of silicalite is about 5 to 6 Angstrom units and its pore volume is 0.18±0.02 cc./gram as determined by adsorption.

The pores of the silicalite particles have a pattern providing for easy access to vapors and liquids intended to be reacted. For example the pores may be in the form of zig-zag channels cross-linked by straight channels.

The preparation of silicalite may be accomplished, for example by the hydrothermal crystallization of a reaction mixture comprising water, a source of silica and an alkylonium compound at a pH of 10 to 14 to form a hydrous crystalline precursor, and subseqently calcining that precursor to decompose alkylonium moieties present therein. The preparation procedures are described in greater detail in U.S. Pat. No. 4,061,724.

The silicalites contemplated for use in this invention generally contain about 700 to 14,000 ppm of alumina corresponding to a $SiO_2$ to $Al_2O_3$ ratio of about 120 to 2450, preferably about 5000 to 7000 ppm of alumina corresponding to a $SiO_2$ to $Al_2O_3$ ratio of about 240 to 340. The amount of alumina in the silicalite will generally depend to a large extent on the source of silica. For example, commercially available silica sols can typically contain from 500 to 700 ppm $Al_2O_3$ whereas fumed silicas can contain from 80 to 2000 ppm of $Al_2O_3$. Silicalites containing still larger amounts of alumina may be obtained by using other sources of silica with higher contents of alumina as is well-known in the art.

Still another class of pentasil-type silicates which may be utilized as the catalyst in the process of this invention are crystalline borosilicates as described for example in previously-cited U.S. Pat. No. 4,285,919 of Klotz et al, the entire disclosure of which is incorporated by reference. The foregoing crystalline borosilicate materials, which are identified as AMS-1B borosilicates have a particular X-ray powder diffraction pattern as is shown hereinafter. Such a crystalline borosilicate can generally be characterized, in terms of the mole ratios of oxides, as follows in Expression I:

$$0.9 \pm 0.2\ M_{2/n}O:B_2O_3:YSiO_2:ZH_2O \qquad (I)$$

wherein M is at least one cation, n is the valence of the cation, Y is within the range of 4 to about 600, and Z within the range of 0 to about 160, or more.

In another instance, a crystalline borosilicate can be represented in terms of mole ratios of oxides for the crystalline material not yet activated or calcined at high temperatures as follows in Expression II:

$$0.9 \pm 0.2(WR_2O + [1-W]M_{2/n}O):B_2O_3:YSiO_2:ZH_2O \quad (II)$$

wherein R is an alkylammonium cation, M is at least one cation, n is the valence of the cation M, Y is a value within the range of 4 to about 600, Z is a value within the range of 0 to about 160, and W is a value greater than 0 and less than 1.

In Expression I, M can represent an alkali-metal cation, an alkaline-earth-metal cation, an ammonium cation, an alkylammonium cation, a hydrogen cation, a catalytically-active-metal cation, or mixtures thereof. In Expression II, M can represent an alkali-metal cation, an alkaline-earth-metal cation, an ammonium cation, an alkylammonium cation, a hydrogen cation, a catalytically-active metal cation, or mixtures thereof.

Advantageously, the value for Y falls within the range of 4 to about 500. Suitably, Y is within the range of 4 to about 300; preferably, within the range of about 80 to about 120.

Suitably, Z is within the range of 0 to about 40.

The original cation "M" in the above expressions can be replaced, at least in part, in accordance with techniques well known in the art by ion exchange with other cations. Preferred replacing cations include tetraalkylammonium cations, metal ions, ammonium ions, hydrogen ions, and mixtures of the above. Particularly preferred cations are those which render the AMS-1B crystalline borosilicate more catalytically active. These materials include hydrogen, rare earth metals, aluminum, and other catalytically active materials and metals known to the art. The catalytically active components can be present in an amount from about 0.05 to about 25 weight percent of the AMS-1b crystalline borosilicate.

Members of the family of AMS-1B crystalline borosilicates possess a specified and distinguishing X-ray powder diffraction pattern, which can be obtained by means of X-ray powder diffraction measurements.

In order to facilitate the reporting of the results obtained, the relative intensities i.e., relative peak heights, were arbitrarily assigned the values shown in Table IV.

TABLE IV

| Relative Peak Height | Assigned Strength |
|---|---|
| less than 10 | VW (very weak) |
| 10–19 | W (weak) |
| 20–39 | M (medium) |
| 40–70 | MS (medium strong) |
| greater than 70 | VS (very strong) |

These assigned strengths are used hereinafter.

In the following table, interplanar spacings are represented by "d" and are expressed in terms of Angstrom units (A) or nanometers (nm). The relative intensities are represented by the term "I/Io" and the term "assigned strength" is represented by "A.S."

The AMS-1B crystalline borosilicates provide an X-ray diffraction pattern comprising the X-ray diffraction lines and assigned strengths as shown in Table V:

TABLE V

| d. A | d. nm | A.S. |
|---|---|---|
| 11.2 ± 0.2 | 1.12 ± 0.02 | W-VS |
| 10.0 ± 0.2 | 1.00 ± 0.02 | W-MS |
| 5.97 ± 0.07 | 0.597 ± 0.007 | W-M |
| 3.82 ± 0.05 | 0.382 ± 0.005 | VS |
| 3.70 ± 0.05 | 0.370 ± 0.005 | MS |
| 3.62 ± 0.05 | 0.362 ± 0.005 | M-MS |
| 2.97 ± 0.02 | 0.297 ± 0.002 | W-M |

TABLE V-continued

| d. A | d. nm | A.S. |
|---|---|---|
| 1.99 ± 0.02 | 0.199 ± 0.002 | VW-M |

By simple regulation of the quantity of boron (represented as $B_2O_3$) in the preparation mixture, it is possible to vary the $SiO_2/B_2O_3$ molar ratio in the final product in a range of about 40 to about 600, or more. In instances where an effort is made to minimize aluminum in the borosilicate crystal structure, the molar ratios of $SiO_2/Al_2O_3$ can easily exceed a ratio of 2000:1 to 3000:1, or more. This ratio is generally only limited by the availability of aluminum-free raw materials.

In general, the surface area of the AMS-1B crystalline borosilicate, as determined by BET surface area analysis, falls within the range of about 300 m²/gm to about 450 m²/gm and the particles of the borosilicate have a maximum diameter, as determined by a scanning electron microscope, of about 2 microns.

Procedures for the preparation of the basic AMS-1B borosilicates and various calcination and ion-exchange techniques are described in greater detail in U.S. Pat. No. 4,285,919.

Examples of lower alkyl, or phenyl ethers which are contemplated to be reacted under this invention are, for example anisole and phenetole. The preferred reactant is anisole which yields 2-cresol as the preferred product.

The reaction may be carried out in vapor or liquid state under a wide variety of conditions. Reaction temperatures may be employed, for example in the range of about 160° to 350° C., preferably about 200° to 300° C. The pressure is generally uncritical to the reaction and subatmospheric, atmospheric or superatmospheric pressures may be employed. In most cases, however, the pressure of the reaction will be in the range of about 1 to 20 atmospheres absolute.

If the lower alkyl phenyl ether feed is in the vapor state at the reaction temperature, then it can be fed in undiluted state or diluted with a relatively inert carrier gas, such as nitrogen, argon, helium, and the like. Likewise, if the reactant is liquid at the reaction temperature, then it also can be used either alone or with a suitable diluent.

Water may be present in the reactant feed stream. If water is utilized, its amount can range from about 0.5 mole up to about 2 moles of water per mole of ether feed and, preferably, ranges from about 1 to 2 moles of water per mole of ether feed.

Contact or residence time can also vary widely, depending upon such variables as the identity of the ether feed, catalyst, reactor, temperature and pressure. Typical contact times range from a fraction of a second to more than several hours when a catalyst system other than a fixed bed is used, with preferred contact times, at least for vapor phase reactions, between about 0.5 and 200 seconds. Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the pentasil catalyst in conjunction with an inert material such as glass wool to regulate the pressure drop of the reactant stream through the catalyst bed and the contact time of the reactant compounds with the catalyst particles. The following examples are illustrative embodiments of this invention. The catalyst utilized was an H-ZSM-5 zeolite or a silicalite. The H-ZSM-5 zeolite was prepared by replacing with hydrogen ions all but 500 ppm based on the weight of the zeolite of the sodium ions in a sodium aluminosilicate ZSM-5 catalyst prepared in accordance with U.S. Pat. No. 3,702,886, in which the ratio of silica to alumina was about 12.

The silicalite used was sold by Union Carbide Corporation under the designation "S-115." It was prepared as described in U.S. Pat. 4,061,724 and was composed of more than 99 wt. % of silica containing about 6500 to 7000 ppm of alimina such that the $SiO_2$ to $Al_2O_3$ ratio was about 241 and the catalyst contained about 0.03 wt. % of the total of sodium and potassium.

The crystal structure of the silicalite was made up of a tetrahedral framework, which contained a large fraction of five-membered rings of silicon-oxygen tetrahedra. Its channel system was composed of near-circular zig-zag channels (free cross-section 5.4±0.2A) cross-linked by elliptical straight channels with a free cross-section of 5.75×5.15 A. Both channels were defined by 10 rings. The X-ray powder diffraction pattern was as defined in Table A of U.S. Pat. No. 4,061,724.

Other properties of the silicalite were a pore volume of about 0.19 cc/gm and a crystal density of about 1.76 cc/gm.

Varying amounts of one of the foregoing catalysts in conjunction with about 1.2–1.3 g of glass wool was charged to an oil heated 14 in. tubular reactor having an inside diameter of about ¼ inch. About 8 ml/hr of reaction feed liquid consisting of reagent grade anisole or phenetole were evaporated and charged to the reactor with varying amounts of helium carrier gas at reaction conditions. The vapor effluent was condensed in an ice cooled trap and collected. After four hours the liquid feed was stopped and the passage of helium carrier gas was continued for another 1 ½ hours to yield a product condensate.

EXAMPLES 1 TO 3

The foregoing procedure was followed using reagent grade anisole as the feed compound.

Specific values for reaction conditions which varied among the examples including catalyst weight, average reaction temperature and pressure and helium flow, contact time, and the results of the GC product analysis are shown in Table VI. Values for percent conversion of anisole were calculated by dividing the moles of total product times 100 by the moles of anisole fed. The selectivity was calculated by dividing the percent conversion to the indicated compound by the precent conversion to total products.

TABLE VI

| Example | 1 | 2 | 3 |
| --- | --- | --- | --- |
| Catalyst | S-115 | H-ZSM-5 | H-ZSM-5 |
| Catalyst Weight (g) | 7.46 | 4.92 | 4.86 |
| Av. Reaction Temp. (°C.) | 300.7 | 307.0 | 250.4 |
| Av. Reaction Press. (atm) | 8.7 | 7.4 | 7.9 |
| Av. He Flow (ml/min.) | 161.6 | 232.0 | 277.0 |
| Contact Time (secs.) | 11.9 | 8.0 | 7.0 |
| Conv of Anisole (%) | 11.0 | 1.7 | 1.0 |
| Selectivity (%) | | | |
| Phenol | 87.0 | 89.0 | 93.0 |
| 2-Cresol | 10.0 | 9.0 | 5.5 |

TABLE VI-continued

| Example | 1 | 2 | 3 |
| --- | --- | --- | --- |
| 4-Cresol | 3.0 | 2.0 | 1.5 |

The results shown in Table VI indicate that the selectivites of the reaction for 2-cresol were in all cases at least 3 times those for 4-cresol, which was the only other cresol produced in detectable amount.

EXAMPLES 4 TO 6

The general procedure of Examples 1 to 3 was followed except that the feed compound was phenetole (ethyl phenyl ether). Reaction conditions and results of the GC analysis of the product are shown in Table VII:

TABLE VII

| Example | 4 | 5 | 6 |
| --- | --- | --- | --- |
| Catalyst | H-ZSM-5 | H-ZSM-5 | S-115 |
| Catalyst Weight (g) | 4.82 | 4.81 | 7.57 |
| Av. Reaction Temp. (°C.) | 253.0 | 252.5 | 252.3 |
| Av. Reaction Press. (atm) | 8.0 | 8.0 | 10.7 |
| Av. He Flow (ml/min.) | 318.4 | 304.0 | 38.3 |
| Contact Time (secs.) | 6.3 | 6.1 | 49.4 |
| Conv. of Phenetole (%) | 1.0 | 1.0 | 12.0 |
| Selectivity (%) | | | |
| Phenol | 2.4 | 9.0 | 42.4 |
| 2-Ethylphenol | 4.0 | 11.0 | 6.3 |
| 4-Ethylphenol | — | 2.3 | 4.1 |
| unknowns | 93.6 | 77.7 | 47.2 |

The results shown in Table VII indicate that the selectivity of the reaction for 2-ethylphenol was in all cases considerably higher than that for 4-ethylphenol, the only other ethylphenol detected.

I claim:

1. A process for the production of a 2-lower alkyl phenol having the formula:

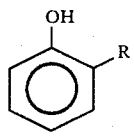

wherein R is lower alkyl, by transalkylation of a lower alkyl phenyl ether having the formula:

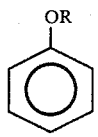

comprising contacting a feed stream comprising said lower alkyl phenyl ether at an elevated temperature with a medium-pore, pentasil-type molecular sieve as catalyst.

2. The process of claim 1 wherein said catalyst is a ZSM-5 zeolite catalyst having the formula:

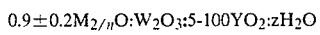

$0.9 \pm 0.2 M_{2/n}O:W_2O_3:5\text{-}100YO_2:zH_2O$ wherein M is a cation, n is the valence of said cation, W is selected from the group consisting of aluminum and gallium, Y is selected from the group consisting of silicon and germanium, and z is from 0 to 40, and in which at least about 80% of the cations are replaced with hydrogen ions.

3. The process of claim 2 wherein said ZSM-5 zeolite has an X-ray diffraction pattern with lines as shown in Table II of the specification.

4. The process of claim 3 where said catalyst has the formula:

$$0.9\pm0.2 M_{2/n}O:Al_2O_3:5-100SiO_2:zH_2O$$

and M is selected from the group consisting of alkali metal cations and tetraalkylammonium cations, the alkyl groups of which contain 2-5 carbon atoms.

5. The process of claim 4 wherein the ratio of $SiO_2$ to $Al_2O_3$ in said catalyst is in the range of about 10 to 30.

6. The process of claim 1 wherein said catalyst is a silicalite containing about 700 to 14000 ppm of alumina, which catalyst has been calcined from the as synthesized form at least once.

7. The process of claim 6 wherein said calcined silicalite contains about 5000 to 7000 ppm of alumina.

8. The process of claim 6 wherein said calcined silicalite has a mean refractive $\pm 0.01$ and a specific gravity at 25° C. of $1.70\pm0.08$.

9. The process of claim 6 wherein the six strongest d-values of the X-ray pattern of said calcined silicalite are as set forth in Table III of the specification.

10. The process of claim 1 wherein said catalyst is an AMS-1B borosilicate.

11. The process of claim 10 wherein said catalyst has the formula $$0.9\pm0.2\ M_{2/n}O:B_2O_3:YSiO_2:ZH_2O \quad (1)$$

wherein M is at least one cation, n is the valence of the cation, Y is within the range of 4 to about 600, and Z is within the range of 0 to about 160.

12. The process of claim 11 wherein the catalyst has an X-ray diffraction pattern as indicated in Tables IV and V of the specification.

13. The process of claim 1 wherein R is methyl, ethyl, n-propyl or n-butyl.

14. The process of claim 13 wherein said lower alkyl phenyl ether is anisole and said 2-lower alkyl phenol is 2-cresol.

15. The process of claim 13 wherein said lower alkyl phenyl ether is phenetole and said 2-lower alkyl phenol is 2-ethylphenol.

16. The process of claim 1 wherein said reaction occurs in the vapor phase and said elevated temperature is in the range of about 160° to 350° C.

17. The process of claim 16 wherein said temperature is in the range of about 200° to 300° C.

18. The process of claim 16 wherein said catalyst is in the form of a fixed bed and said feed stream into said bed also contains an inert carrier gas.

* * * * *